(12) United States Patent
Putz et al.

(10) Patent No.: US 8,333,588 B2
(45) Date of Patent: Dec. 18, 2012

(54) MEDICAL OR DENTAL HAND-PIECE ELEMENT

(75) Inventors: Stefan Putz, Salzburg (AT); Stephan Rauchenzauner, Signature Park (SG); Norbert Schatz, Bürmoos (AT); Karl Schmiedlechner, Ostermiething (AT); Hannes Wagner, Salzburg (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 349 days.

(21) Appl. No.: 12/011,142

(22) Filed: Jan. 23, 2008

(65) Prior Publication Data

US 2008/0176181 A1 Jul. 24, 2008

(30) Foreign Application Priority Data

Jan. 24, 2007 (EP) ..................................... 07001444

(51) Int. Cl.
*A61C 1/00* (2006.01)
(52) U.S. Cl. ............................ 433/131; 433/114; 310/46
(58) Field of Classification Search .................. 433/133, 433/103, 114, 131; 310/154.01, 105, 50, 310/47, 49.28, 46; 362/119; 464/18, 30, 464/182, 901; 408/172; 173/216–218, 222, 173/164; 606/80, 167–189
See application file for complete search history.

(56) References Cited

U.S. PATENT DOCUMENTS

| | | | | |
|---|---|---|---|---|
| 3,900,952 A | * | 8/1975 | Landgraf et al. | 433/133 |
| 4,260,381 A | * | 4/1981 | Eibofner et al. | 433/126 |
| 4,564,781 A | * | 1/1986 | Arnegger | 310/208 |
| 4,678,922 A | * | 7/1987 | Leininger | 290/54 |
| 4,725,232 A | | 2/1988 | Hatakeyama | |
| RE36,917 E | * | 10/2000 | Leininger | 290/54 |
| 6,132,213 A | * | 10/2000 | Knorpp et al. | 433/131 |
| 6,270,342 B1 | | 8/2001 | Neuberger et al. | |
| 7,095,142 B2 | * | 8/2006 | Leininger | 310/47 |

FOREIGN PATENT DOCUMENTS

DE 100 66 004 12/2001
FR 1 009 957 6/1952

OTHER PUBLICATIONS

Translation of FR19520605. Translated by the McElroy Company, Jun. 2010.*
European Search Report for EP07 00 1444 (mailed Jun. 20, 2007).

* cited by examiner

*Primary Examiner* — Cris L Rodriguez
*Assistant Examiner* — Edward Morgan
(74) *Attorney, Agent, or Firm* — Klarquist Sparkman, LLP

(57) ABSTRACT

There is disclosed a medical or dental hand-piece element comprising a coupling mechanism for a detachable connection of the hand-piece element to a drive unit, a tool receptacle that is or can be connected to the hand-piece element, and a drive element for transmitting a driving movement from the drive unit to the tool receptacle so that the tool receptacle can be set into a working movement, wherein the drive element comprises at least one rotatable shaft, and a generator for converting mechanical energy into electric energy, wherein the generator can be driven by the at least one rotatable shaft of the drive element.

39 Claims, 5 Drawing Sheets

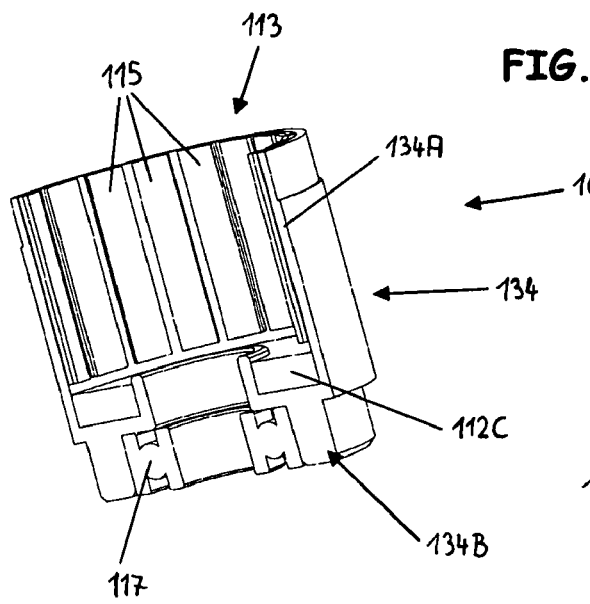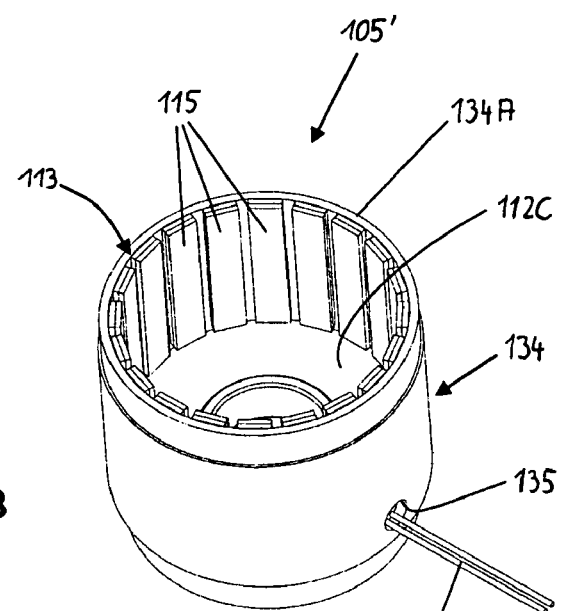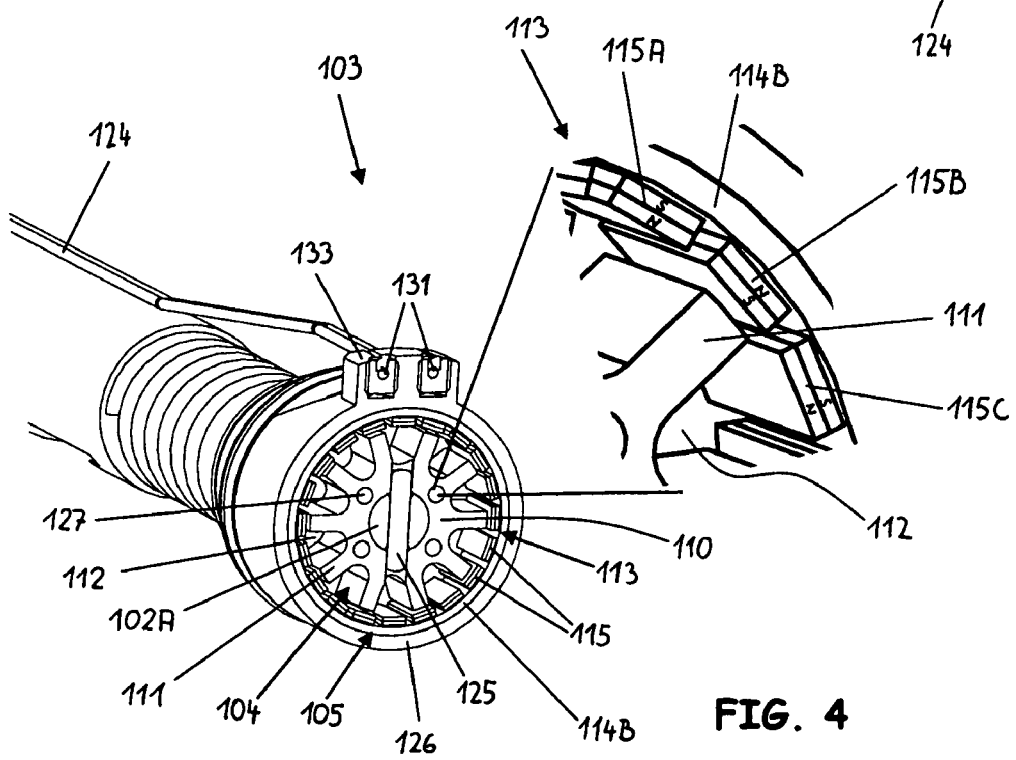

MEDICAL OR DENTAL HAND-PIECE ELEMENT

CROSS REFERENCE TO RELATED APPLICATION

The present application claims priority from pending European Patent Application No. 07001444.4, filed Jan. 24, 2007, which is incorporated herein by reference.

BACKGROUND

1. Field

The present invention relates to a medical or dental hand-piece element comprising a generator for converting mechanical energy into electric energy.

2. Description of Prior Art

U.S. Pat. No. 6,270,342 describes dental hand-pieces having generators, whereby the generators are driven by a fluid that is sent from an external fluid source via a corresponding connection on the hand-piece and a line through the hand-piece to the generator. The generator supplies electric power to various consumers for their operation, e.g., a laser, a drive for a dental tool, a light source, an ultrasonic or microwave generator.

There are many hand-pieces for various medical and dental applications that do not have a connection to an external fluid source. Although other hand-pieces have a connection to an external fluid source, e.g., to a compressed air source, the fluid supplied to the hand-piece is needed for other purposes and/or the flow rate of fluid supplied to the hand-piece, the fluid pressure or the energy content of the fluid are too low to drive a generator.

Therefore, one object of the present approach is to create a hand-piece or a hand-piece element having an alternative drive mechanism for the generator, so that no drive fluid need be supplied to the hand-piece or the hand-piece element for operation of the generator.

SUMMARY

According to one embodiment the medical or dental hand-piece element is provided with a coupling mechanism for detachable connection of the hand-piece element to a drive unit, a tool receptacle that is or can be connected to the hand-piece element and a drive element for transfer of a driving movement from the drive unit to the tool receptacle so that a working movement can be induced on the tool receptacle. The drive element comprises at least one rotatable shaft which is connected directly or indirectly to the generator and drives the generator. Generators may thus also be operated in hand-piece elements without a suitable fluid supply or with no fluid supply. Generators are understood below to refer to electrodynamic converters for converting mechanical energy into electric energy.

The rotor of the generator or the entire generator is preferably arranged coaxially with at least one shaft of the drive element. Thus, in an advantageous manner, the number of bearings for supporting the shaft and the rotor is reduced and in particular both components can be supported by just two roller bearings. In addition, due to the coaxial design the diameter of the hand-piece element can be kept as small as possible, so that the hand-piece element can be handled easily.

Hand-piece elements often have a drive element having multiple shafts or shaft parts which are interconnected by gear wheels or gears, for example. The shafts usually run essentially one after the other through the hand-piece element so that a first shaft is arranged closer to the coupling mechanism than a second shaft. In this design, the generator is preferably arranged around the first shaft so that it can be removed easily through the opening in the coupling mechanism in particular for maintenance or for replacement in the event of damage. Another advantage of this arrangement is the simplified manufacturing process for various hand-piece elements with different gears because with the arrangement of the generator on the first shaft and thus upstream from the gear, the same rotational speed range prevails with all the hand-piece elements so the same generator can be used.

The coupling mechanisms of hand-piece elements are often equipped with a receptacle element, in particular a coupling tube to receive a coupling counterpart. As an alternative or in addition to the arrangement of the generator around the first shaft, the generator may be arranged at least partially in or on the receptacle element or in or on a continuation of the receptacle element. Since the receptacle element is usually very easily detachable from the hand-piece element through the opening of the coupling mechanism, removal or replacement of the generator is thus additionally facilitated.

The term hand-piece element refers to straight hand-pieces or handles, curved hand-pieces or handles, which are often referred to as contra-angle hand-pieces in the dental field, as well as parts of hand-pieces. Such parts may be formed, for example, by a gripping section of a hand-piece which can be connected to various head sections for different tools or to gears for different step-down or step-up gear ratios. The parts of hand-pieces may also be designed as intermediate pieces, couplings, adaptors or independent sleeve sections, for example.

The generator may be used to supply electric power to one or more consumers (i.e., power consuming devices), e.g., a diode laser, a drive for a dental tool, a lighting device, an ultrasonic or microwave generator, an analgesia apparatus, measurement sensors, e.g., for measuring temperatures, acceleration, torque, rotational speed or sound level, microphones, actuators, e.g., piezoelectric elements for vibration damping, circuits for processing data or measured values, control and/or regulating circuits, data transmission devices and transmitters, devices for recognizing or detecting tools or instruments that can be connected to the hand-piece element and screens or displays. In a preferred embodiment, the generator operates a lighting device with at least one optical semiconductor component, in particular with at least one light-emitting diode (LED) which emits light with a wavelength of approximately 370-800 nm, which is visible to the human eye.

One disadvantage of supplying electric power to a lighting device by a generator operated by a shaft of the drive element of the hand-piece element is the constant changes in power output by the generator due to the change in the rotational speed of the shaft during the medical treatment. Incandescent lamps are usually used in hand-piece elements for lighting the preparation site which have a noticeable shift in color temperature of the radiation spectrum emitted, especially when operated below the power rating. The result is a noticeably inferior lighting of the preparation site for the user and a change in the subjective color perception. The object is thus to create a lighting device which is more suitable for operation with an electric power source having a fluctuating power supply, in particular a generator. This is achieved by using one or more optical semiconductor components, in particular a white light LED as the lighting means, because the color temperature of the white light LEDs is relatively constant during operation at a power below the rated power in comparison with incandescent lamps and LEDs are less sensitive to a fluctuating power supply. Therefore, a more uniform lighting is achieved regardless of the rotational speed of the shaft of the hand-piece element.

In a special embodiment, the LED additionally comprises a color conversion material to convert the wavelength of the radiation emitted by the LED chip, in particular into white light. Such color conversion materials may contain, for example, luminescent dyes which are stimulated to luminescence by blue light and emit yellow light. If only a portion of the emitted blue radiation is converted to yellow light, then the additive mixture of the two colors yields a white light. For example, orthosilicates or YAG dyes may be used as the color conversion materials.

A first embodiment relates to a surgical hand-piece element, in particular a dental-surgical hand-piece element. These surgical hand-piece elements have a coupling mechanism at one end by means of which they can be connected to a drive unit, in particular an electric motor. The drive unit is connected by a line to a control and/or regulating unit which controls and/or regulates operation of the drive unit and the hand-piece element and by means of which the user can often select additional different operating programs for the drive unit and the hand-piece element or can adjust or change individual operating parameters and which additionally often drives a pump which conveys sterile fluid out of the fluid container or bag to the treatment site. The control and/or regulating unit usually also comprises a foot control, in addition to actuator elements for selecting the operating programs or operating parameters. The control and/or regulating unit is connected to a power source by a cable. The hand-piece element, the drive unit and the control and/or regulating unit together thus form a compact and portable surgical treatment device, i.e., one that is easily transported by a single person from a first site to a second site, requiring only connection to an electric power source for its operation.

Surgical hand-piece elements, in particular dental-surgical hand-piece elements are frequently used to perform especially difficult procedures requiring a high level of precision, in particular the insertion of implants into tissue, e.g., dental implants into the jawbone. These procedures often require that special conditions be observed or that special prerequisites be met, e.g., applying a higher torque in comparison with other medical treatments, a very cautious and slow procedure of at least certain treatment steps or visual monitoring of the insertion of the implant by the user of the hand-piece element. To be able to meet these conditions, surgical hand-piece elements, in particular dental-surgical hand-piece elements are usually operated with a motor speed range from approximately 3,000 to 50,000 revolutions per minute (rpm), with the speed range between approximately 3,000 and approximately 20,000 rpm being extremely low for medical hand-piece elements.

In integration of a generator into a surgical hand-piece element, in particular a dental-surgical hand-piece element, the additional challenge is therefore to design the generator which is driven by the shaft of the drive element in such a way that it delivers enough power to operate the consumer even at rotational speeds of the shaft and thus also of the rotor connected to the shaft of at least approximately 3,000 rpm. The power output should in particular be great enough to operate a lighting device comprising one or more optical semiconductor components, in particular one or more LEDs. To obtain a light intensity of approximately 11 kLux, which is enough for the surgical application, the power output by the generator that can be consumed by the LED should be at least approximately 110 mW per LED.

In the upper speed range of the surgical hand-piece element, in particular the dental-surgical hand-piece element, especially at speeds in excess of approximately 30,000 rpm, there is also the requirement that the power delivered by the generator must not be too great, which would cause the consumer that is supplied with electric power by the generator to be destroyed or damaged or its lifetime to be greatly shortened.

In supplying LEDs with power from the generator, another factor to be taken into account is that the generator supplies an alternating current. Since LEDs have preferred directions of current flow, the alternating current may either be converted to direct current via known electric or electronic rectifiers or the LED may preferably be operated with an alternating current beyond the so-called flicker frequency (corresponding at least to approximately 25 Hz A.C. voltage) above which the human eye perceives a constant uninterrupted emission of light. Thus only every second half wave of the sinusoidal alternating current and only a portion of the power generated by the generator can be used by the LED for generating light but it is advantageous that no rectifier is needed in this embodiment.

To solve this problem, in a first embodiment there is the possibility of using a generator for the hand-piece element that provides enough energy for the consumer in the lower speed range. In the high-speed range in particular, excess energy generated by the generator is stored in an energy storage mechanism, e.g., a rechargeable battery, a capacitor or an inductor and later made available to one or more consumers. Electric or electronic components may optionally also be provided to process the power delivered by the energy storage mechanism for the respective consumer. The consumer may in turn preferably be one or more LEDs. This embodiment has the additional advantage that power may be supplied to one or more consumers independently of operation of the generator so that the lighting device, for example, can be operated even if the generator is producing little or no energy. In a preferred embodiment, a circuit which supplies the lighting device with power for 5-60 seconds, in particular 15-30 seconds after stopping the generator is provided so that the user can illuminate the preparation site during pauses in treatment or after the end of the treatment.

As an alternative or in addition to accommodating an accumulator (battery) in the hand-piece element, in a second embodiment one or more devices may be provided for dissipating at least some of the excess energy generated by the generator in the hand-piece element. These devices may be various electric and/or electronic components, e.g., Z-diodes, step-down converters, resistors or voltage regulators with several transistors.

Installation of a battery and accommodation of devices for dissipating energy involves several disadvantages, however: in particular the dimensions of the dental-surgical hand-piece element are very small due to the fact that it must be used in the oral cavity, so there is hardly any room for accommodating additional components in addition to the generator. The devices for dissipating energy also generate substantial quantities of heat so that there is a need for dissipating at least some of this heat because otherwise the hand-piece element will heat up to such an extent that the user could no longer hold the hand-piece element in his/her hand. Furthermore, batteries cannot be sterilized repeatedly.

There is thus the object of designing a generator for a surgical hand-piece element, in particular a dental-surgical hand-piece element such that the generator will have the most optimal possible power performance, i.e., it will yield a sufficient power to operate the consumer(s), in particular at least one LED, at rotational speeds of the rotor of approximately 3,000 revolutions per minute and so that with an increase in rotational speed, the increase in power output will decline, so that no additional energy-dissipating devices or energy storage mechanisms are required.

To achieve this object, the generator in a preferred third embodiment of a surgical hand-piece element, in particular a dental-surgical hand-piece element, has a stator and a rotor connected either directly or indirectly to the rotatable shaft of the drive element, whereby the rotor comprises a magnetic yoke element or a magnetic flux element. The magnetic flux element preferably consists of a central body with several protrusions extending away from it radially, separated from one another by interspaces. The generator also has a magnetic element, which may comprise multiple individual permanent magnets, the individual magnets being arranged in a rotationally symmetrical arrangement and with alternating polarities. Alternatively, the magnetic element may comprise a closed magnetic ring, e.g., a pressed or sintered magnetic ring which is magnetized with an alternating polarity section by section, so that the magnetic ring has multiple permanent magnet ranges. Preferably the number of permanent magnets or the permanent magnet ranges is twice as great as the number of radial protrusions on the magnetic flux element of the rotor. The stator preferably comprises at least one coil and one magnetic element. It may optionally also have at least one other magnetic flux element.

During operation of the hand-piece element, rotation of the magnetic flux element of the rotor is induced, so that a magnetic flux through the permanent magnets or permanent magnet areas of the same polarity is alternately induced over the magnetic flux element(s), in particular the protrusions of the magnetic flux element of the rotor and through the coils, thus building up an alternating field and inducing an alternating voltage. With a generator of such a design, it is surprisingly possible to achieve a performance curve that adequately fulfills the requirements specified above, in particular an adequate release of power at low rotational speeds and a reduced output of power at higher rotational speeds. Therefore it is not necessary to install additional energy-dissipating devices or energy storage mechanisms in the hand-piece element.

In an especially preferred embodiment, the surgical hand-piece element, in particular the dental-surgical hand-piece element is provided with a lighting device comprising an LED in particular. The generator of this hand-piece element has an air gap of approximately 0.12 mm-0.35 mm, preferably 0.18 mm-0.32 mm, especially preferably 0.24 mm-0.28 mm. The magnetic element of this generator comprises 16 to 24 individual magnets or magnet regions, preferably 20 individual magnets or magnet regions, which corresponds to ten pole pairs. Accordingly the magnetic flux element of the rotor comprises eight to twelve protrusions, preferably ten protrusions. The magnetic element has a length of approximately 4 mm-9 mm, preferably approximately 5 mm-7 mm, especially preferably 6 mm-7 mm and a thickness of less than approximately 0.7 mm, preferably less than 0.5 mm. The width of an individual magnet amounts to less than approximately 1.5 mm, preferably less than approximately 1.3 mm. The magnetic remanence of the entire magnetic element amounts to approximately 1,000 to 1,500 mT, preferably approximately 1,100 to 1,200 mT. In addition, two coils connected in series are provided, with the number of windings per coil amounting to approximately 80 to 130 windings, preferably 110 to 120 windings. As an alternative, it is also possible to provide just one coil. The dimensions of the coils are approximately 13 mm×7 mm×1.5 mm, preferably approximately 10.2 mm×5 mm×1 mm. With this design the power output of the generator is limited to approximately 1 watt maximum power without having to use electric or electronic components or devices for dissipating excess energy here. An optimal power supply to the one LED is thus implemented, so the one LED is not supplied with an excessively high power supply, in particular at high rotational speeds of the rotor, which would shorten the lifetime of the LED. The illumination intensity of the LED is thus limited to approximately 35 kLux so that light that is too glaring for the human eye is not emitted to the preparation site.

Due to this design, another advantage achieved is that the power loss by the generator is minimized, amounting to a maximum of approximately 1.5 watt. This ensures that even with prolonged operation, heating of the generator and the hand-piece element will not be so great that the user of the hand-piece element can no longer hold it in his/her bare hand.

Another second embodiment relates to a medical hand-piece element, in particular a dental-medical hand-piece element. The generator of this hand-piece element has a rotor and a stator, wherein the rotor comprises a magnetic element that is attached to the at least one rotatable shaft of the drive element. The advantage of this generator lies in its simple and inexpensive production. However because of the small diameter of the hand-piece element which cannot be enlarged at will, there is a problem with this design in making available an adequate magnetic field strength, so that the generator can deliver enough power for the consumer.

In a first embodiment, the magnetic element is designed as a hollow cylindrical permanent magnet having two or more poles with the rotatable shaft passing through its inner bore. At least a part of this shaft, in particular the part accommodated in the inner bore of the magnetic element, is preferably manufactured from a magnetically conductive material, e.g., steel. Therefore, a better magnetic conduction for the magnetic field of the magnetic element is achieved so that the generator can generate a higher power. Additionally or alternatively, the shaft to which the magnetic element is attached may have a first section with a first diameter and a second section with a second smaller diameter. The magnetic element here is attached to the second thinner section, so that because of the reduced diameter of the second shaft section, the wall thickness of the hollow cylindrical permanent magnet can be increased at the same outside diameter so that a greater magnetic field strength is available and thus a higher power output by the generator can be achieved.

The diameter of the second thinner shaft section preferably amounts to approximately 2-2.5 mm, especially preferably approximately 2.35 mm. Due to this dimension, the wall thickness of the magnetic element can be increased to the extent that there is an increase in the power delivery by the generator, but, on the other hand, the second shaft section still has enough mechanical strength so there is no risk of the second shaft section breaking or being bent, especially in transferring of high torques.

Another problem with this generator is that during operation of the generator a force acts on the magnetic element in the direction of locations of especially high magnetic field density, e.g., in the direction of the pole shoes of the stator. The angular velocity is influenced periodically by this acting force, thus causing resonance or vibration which can have a negative effect on smooth running of the shaft on which the magnetic element is mounted, especially in operation of the hand-piece element at high rotational speeds. For example, if this shaft is connected by gear wheels to another shaft, then this resonance and vibration results in an inferior engagement of the tooth elements of the gear wheels, so that there is an increase in the noise generated by the gear wheels and in the wear on the gear wheels during operation of the hand-piece element in an undesirable manner. Therefore, in a second embodiment, to minimize these negative effects, the at least one shaft of the drive element to which the magnetic element is attached is supported at two bearing points, with the magnetic element being arranged between these two bearing points. The two bearing points, which are formed by two ball bearings in particular, are preferably provided as close to the generator as possible. The arrangement of the magnetic element between the bearing points stabilizes the rotor and reduces the development of resonance and vibration.

The hand-piece elements of the second embodiment are operated in higher drive speed ranges, preferably in the range between 20,000 and 50,000 rpm, where the operating time is often longer than that with the surgical hand-piece elements described above. The result may be greater heating of the generator, so that measures must be taken to dissipate this heat because otherwise there may be excessive heating of the handle sleeve of the hand-piece element, which would be unpleasant for the user.

In a third embodiment, the hand-piece element is equipped with a cooling device for dissipating heat generated by the generator. The cooling device may comprise, for example, active or passive heat sinks, heat pipes with a heat transfer medium that evaporates and condenses in their interior, heat-conducting pastes or pads or other known heat-conducting devices. The disadvantage of this embodiment is that additional cooling devices or cooling elements must be provided in the hand-piece element, but there is hardly any space in dental hand-piece elements in particular to accommodate any additional component in addition to the generator.

In a fourth preferred embodiment, the hand-piece element or parts thereof are therefore designed so that they facilitate the dissipation of heat from the generator or they dissipate heat themselves. The coupling device of the hand-piece element or parts thereof, e.g., the receptacle element or the coupling pipe in particular is or can be connected directly or indirectly to the generator, so that a cooling medium can be supplied to the generator through the coupling device. A gas under pressure is preferably used as the cooling medium, especially compressed air which is transferred from the drive unit, e.g., from its coupling element into the receptacle element. If an air-cooled electric motor or a motor operated with compressed gas, for example, is used as the drive unit, then at least a part of this cooling airstream or compressed gas stream may advantageously also be used to cool the generator. At least one air gap in the generator especially preferably is or can be connected to the coupling device so that heat is also dissipated out of the interior of the generator via the cooling medium. Alternatively or additionally, the cooling medium may also be passed by the outside of the generator.

Alternatively or additionally, the coupling device, in particular the receptacle element itself may be used for dissipation of heat. To this end, the generator is connected directly or indirectly to the receptacle element or to a protrusion of the receptacle element or is preferably partially or completely surrounded by it, so that heat generated by the generator is transferred to the receptacle element and is dissipated away from it. The receptacle element and/or its protrusion are also preferably arranged at a distance from the outer sleeve of the hand-piece element, e.g., separated by an air gap so that the transfer of heat to the outer sleeve which comes in contact with the user or the patient is additionally reduced.

If at least one media line is provided in the hand-piece element through which a treatment medium or cooling medium such as water or a water-air mixture is passed, for example, then additionally or alternatively this media line may be arranged to pass by the generator, such that the medium contained therein absorbs and dissipates at least a portion of the heat generated by the generator. The media line may preferably have an enlarged surface area or additional windings for increased transfer of heat in the area of the generator.

The total diameter of the generators described here is less than approximately 15 mm, preferably less than approximately 12 mm, especially preferably approximately 11 mm due to their design. The total diameter of the generator is extremely important for its installation in a medical, in particular a dental hand-piece element because a larger diameter of the hand-piece element should be prevented as much as possible, because a larger diameter would definitely make it more difficult for the user to manage the device and would therefore cause fatigue more rapidly.

To prevent the transfer of microorganisms between patients, it is necessary to sterilize the hand-piece elements after each treatment. Various sterilization methods are used for this, e.g., steam sterilization, chemical sterilization or heat sterilization. If a generator is integrated into a hand-piece element, the generator must be designed so that it resists the conditions prevailing during the various sterilization methods and does so over the entire duration of the sterilization process without any loss of functionality, i.e., the generator must be designed to be sterilizable. In particular, the generator must withstand, without incurring any damage, repeated exposure to an environment with temperatures of at least 120° C., preferably 130° C., especially preferably 134° C. and/or with steam or chemicals or gases, in particular disinfectants, and/or with pressure fluctuations of approximately 1 bar.

To do so, in another preferred embodiment, steels are used for certain components of the generators, e.g., for at least parts of the rotor and/or at least one magnetic flux element, in particular hardenable or hardened steels. When using steels for a magnetic flux element, these steels must also have a sufficient magnetic conductivity. The hardening of the steels can be achieved by various methods, e.g., by hardening and tempering in vacuo or under a protective gas atmosphere. Alternatively, the steels may be provided with coatings such as nickel, chromium, nickel-chromium or plastic, in particular Teflon coatings. Also the magnetic element must be designed to be sterilizable. This may be accomplished either by using corrosion-resistant magnetic materials, e.g., samarium cobalt or by coating the magnetic element, e.g., with nickel or plastics, in particular with Teflon or by encasing the magnetic element, e.g., in a corrosion-resistant steel housing. To make the coil wires sterilizable, they may be equipped with temperature-resistant and/or chemical-resistant insulation, made of enameled wires or coated. The entire stator or at least the coils may also preferably be cast with temperature-resistant and/or chemical-resistant materials, e.g., synthetic resins, in particular with epoxy resin.

Due to this design, the generator together with the hand-piece element can be sterilized. The user is thus not compelled to remove the generator from the hand-piece element before sterilizing. Another advantage of using hardenable and/or hardened steels for components of the generator is their high mechanical load-bearing capacity and excellent material pairing properties. It is thus possible to arrange the rotor coaxially with and directly on the shaft of the drive element, to design the rotor in one piece with the shaft or to mount additional components, in particular gear elements such as gear wheels on the rotor or rotor shaft.

The hand-piece elements are explained in greater detail below on the basis of preferred embodiments and with reference to the accompanying drawings:

BRIEF DESCRIPTION OF THE DRAWINGS

FIGS. 3A and 3B show an alternative embodiment of the stator of the generator from FIG. 1.

FIG. 4 shows a section through the generator along line IV-IV from FIG. 1 with an enlarged detail of a part of the rotor and stator of the generator.

DETAILED DESCRIPTION

Figure 1:
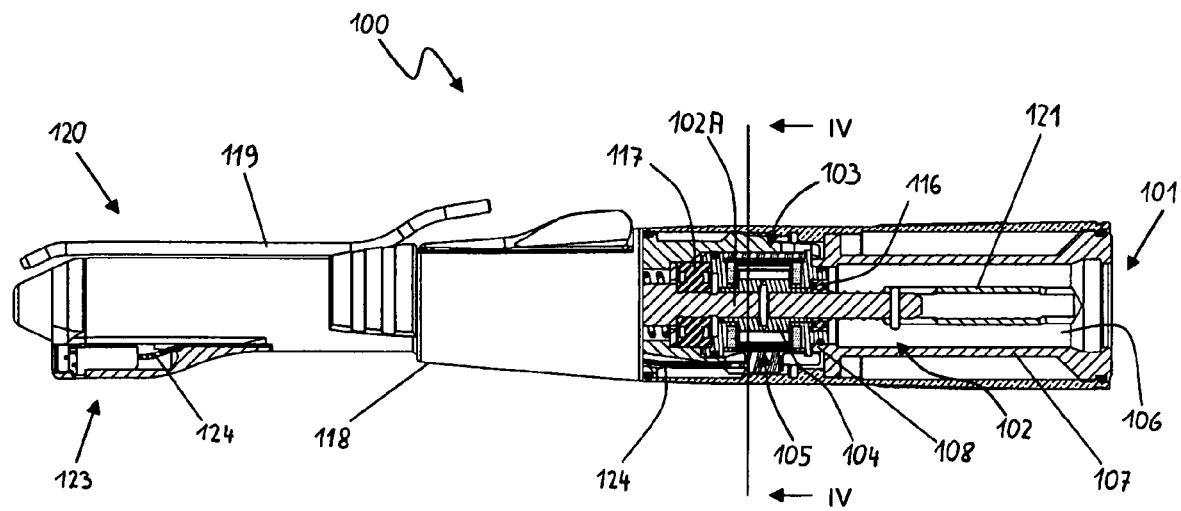
FIG. 1 shows an embodiment of a medical hand-piece element, in particular a dental-surgical hand-piece element, with a generator.

The medical hand-piece element 100 shown in FIG. 1 is designed for surgical applications, in particular dental-surgical applications. It comprises a straight, elongated body having a one-piece or multi-piece outer sleeve 118. A tube 119 which is attached to the outer sleeve 118 can be connected to a fluid source, so that the fluid for cooling and rinsing the treatment site can be dispensed through the tube. The surgical hand-piece element may of course have different external shapes, in particular sections arranged at an angle to one another or a pistol shape.

A tool receptacle into which a treatment tool can be releasably inserted is arranged in a known manner in the distal area or head section 120 of the hand-piece element 100. The tool receptacle is connected to the drive element 102 so that a driving movement, in particular a rotational movement, can be transferred from the drive unit (not shown) to the tool receptacle. The drive element 102 comprises at least one rotatable shaft 102A, but it may also comprise multiple shafts or shaft sections which are connected to one another via gear wheels or step-down or step-up gear ratios.

The connection between the hand-piece element 100 and the drive unit is accomplished via a releasable coupling mechanism 101 which is preferably designed as a plug coupling or a twist-lock plug coupling. The drive unit may be, for example, an air motor or an electric motor, in particular a brushless electric motor. The drive unit may be connected directly to the hand-piece element 100, but it may also be connected indirectly to the hand-piece element 100 via one or more intermediate parts, e.g., adaptors or couplings. The coupling mechanism 101 comprises a receptacle element 106, which is designed as a cylindrical coupling tube 107, for example, to accommodate a coupling counterpart. At least a portion of the shaft 102A is accommodated in the interior of the receptacle element 106, an entraining element 121 is displaceably connected to the shaft 102A and prestressed via a spring 122 (see FIG. 2).

The coupling tube 107 has a protrusion 108 which may be shaped as a cylindrical sleeve, for example. A generator 103 for converting mechanical energy into electric energy is connected to the receptacle element 107 and accommodated at least partially in the protrusion 108 and/or attached thereto. The generator 103 comprises a rotor 104 and a stator 105. The rotatable shaft 102A of the drive element 102 passes through the generator 103, whereby the rotor 104 is directly or indirectly connected to the shaft 102A so that it can be driven by the shaft 102A. The generator 103 and the rotor 104 in particular are arranged coaxially with the shaft 102A. Two bearings 116, 117, preferably designed as ball bearings, support the shaft 102A and the rotor 104. The ball bearings may be designed, for example, as steel, ceramic or hybrid ball bearings with ceramic components. The rotor 104 is preferably arranged between the two bearing points 116, 117, thus achieving the greatest possible stability, so that despite the very small dimensions of the air gaps 128A, 128B, 129 this ensures that the rotor 104 does not come in contact with the stator 105.

In addition, a lighting device 123 is provided in the hand-piece element 100 to emit radiation to the treatment site. The radiation emitted by the lighting device 123 may have wavelengths that are visible to the human eye, but they may also emit other wavelengths either partially or completely, depending on the application. The lighting device 123 preferably includes at least one optical semiconductor component, e.g., an LED. The lighting device is preferably hermetically encapsulated, thus forming an interior space that is completely sealed off from the environment and in which the optical semiconductor component is accommodated. As a result of this measure, the lighting device 123 can also be sterilized.

The lighting device 123 is electrically connected to the generator 103. At least a portion of the electric power generated by the generator 103 is supplied via two electric leads to the lighting device 123 so that the latter emits light as soon as the shaft 102A and thus the rotor 104 of the generator 103 are moving. The lighting device 123 is arranged on the head section 120 of the hand-piece element 100 so that its radiation can be emitted directly, i.e., without the intervention of optical elements such as optical fibers or lenses, in the direction of the treatment site and the tool. As an alternative, however, it is equally possible for the lighting device to be arranged in the interior of the hand-piece element 100 or in a part of the hand-piece element 100 at a distance from the head section and for the light to be carried via optical elements such as glass rods, glass fiber rods or lenses to the head section 120 of the hand-piece element 100 from which it is emitted in the direction of the preparation site.

For cleaning purposes, the surgical hand-piece element 100 can be broken down into several individual parts. To be able to separate the parts of the hand-piece element 100 completely from one another, it is therefore also necessary to design the electric connection between the generator 103 and the connected consumer(s), e.g., the lighting device 123, to be detachable. This may be accomplished, for example, by adding electric plug contacts or sliding contacts to the electric connection between the generator 103 and the consumer.

Figure 2:
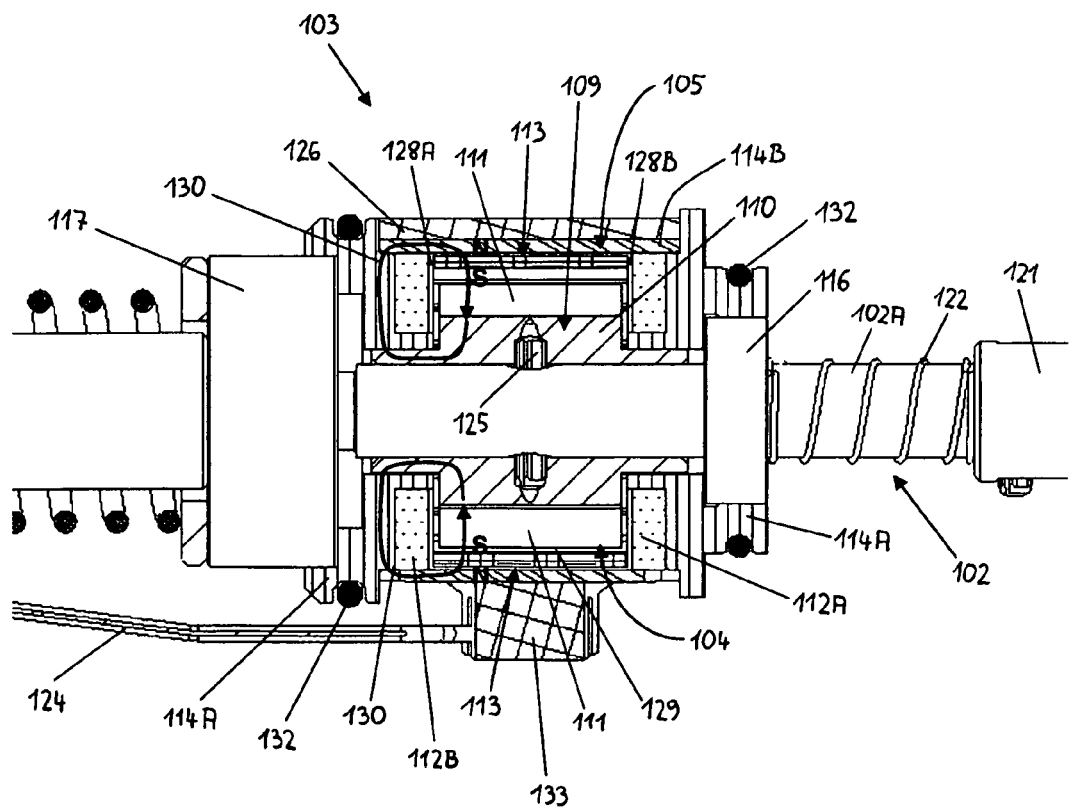
FIG. 2 shows an enlarged representation of the generator of the hand-piece element from FIG. 1.

FIGS. 2 and 4 illustrate the design of the generator 103 and its integration into the hand-piece element 100 in detail. The rotor 104 of the generator 103 comprises a magnetic flux element 109 which preferably has a central body 110 from which several protrusions 111 extend radially, separated from one another by interspaces 112. The body 110 and the protrusions 111 of the magnetic flux element 109 are made of a magnetically conductive material. There is no magnetically conductive material in the interspaces 112. The protrusions 111 are preferably arranged regularly in a rotationally symmetrical arrangement around the cylindrical body 110. The protrusions 111 may be designed as blades or vanes, for example. The body 110 has a borehole passing through it with the shaft 102A of the drive element 102 passing through that. The rotor 104 is fixedly connected to the shaft 102A, e.g., by adhesive bonding, by pressing or by a pin 125. As an alternative, the rotor 104 may also be manufactured in one piece with the shaft 102A.

The stator 105 of the generator 103 comprises two coils 112A, 112B, a magnetic element 113 and two additional magnetic flux elements 114A, 114B. An electric insulator 126, which is made of plastic, for example, and is preferably designed in the form of a sleeve, is provided around parts of the stator 105. The stator 105 and the insulator 126 extend coaxially around the shaft 102A. The number of permanent magnets 115 of the magnetic element 113 is twice as great as the number of radial protrusions 111 of the magnetic flux element 109. The coils 112A, 112B are essentially cylindrical in shape, with their height, i.e., their extent in the axial direction, being smaller than their width, i.e., their diameter in the radial direction. The coils 112A, 112B have a central bore through which the shaft 102A extends and into which at least parts of the rotor 104 and parts of the magnetic flux element 114B protrude.

As shown in FIG. 4 in particular, the magnetic element 113 comprises twenty individual magnets 115 arranged in a rotationally symmetrical pattern around the shaft 102A. Individual magnets 115 arranged side-by-side have an alternating polarity, which means that, as shown in the enlarged detail from FIG. 4 in particular, the north pole points in the direction of the magnetic flux element 114B in the case of an individual magnet 115B whereas in the case of the two neighboring individual magnets 115A, 115C the south pole points in the direction of the magnetic flux element. Opposing individual magnets 115 have the same polarity and thus these same poles are facing one another in the direction of the shaft 102A and/or the magnetic flux element 114B. The magnetic element 113 is separated axially by the air gaps 128A, 128B from the coils 112A, 112B. Another radial air gap 129 separates the magnetic element 113 from the rotor 104.

The magnetic element 113 and the coils 112A, 112B are surrounded axially and/or radially by two magnetic flux elements 114A, 114B made of a magnetically conductive material. The magnetic flux elements 114A, 114B produce the magnetic return of the magnetic lines around and through the coils 112A, 112B as represented schematically by the lines 130 in FIG. 2. The magnetic elements 115 are attached to the magnetic flux element 114B, e.g., by adhesive bonding with synthetic resin, in particular with epoxy resin. The magnetic flux elements 114A each have a borehole through which the shaft 102A passes and into which at least parts of the rotor 104 protrude.

FIG. 4 shows a position of the rotor 104 in relation to the magnetic element 115 in which a magnetic element 115, e.g., magnetic element 115B in the enlarged detail is frontally opposed to one of the protrusions 111, with the two neighboring magnetic elements 115A, 115C being situated in the interspaces 112. All the protrusions 111 are thus opposite only magnetic elements 115 of the same polarity. If rotation of the rotor 104 is induced by the shaft 102A, then the protrusions 111 move further until they are frontally opposite the next oppositely polarized magnetic element 115, e.g., magnetic element 115C. In these two frontal positions, the greatest possible voltage is induced by the magnetic return of the magnetic lines around and through the coils 112A, 112B. In an intermediate position assumed during rotation of the rotor 104, in which position the protrusions 111 are situated between two magnetic elements 115, no voltage is induced because the magnetic lines are not deflected via the magnetic flux elements 114A, 114B through the coils 112A, 112B. Thus alternating magnetic fields are formed by the rotation of the rotor 104 so that the generator 103, driven by the drive element 102, generates an alternating voltage which has an essentially sinusoidal course.

The current generated by the generator 103 is supplied via the free ends of the coils 112A, 112B to electric contact elements 131 and the lines 124 so that a consumer that is or can be connected to the lines, e.g., a lighting device 123 is supplied with electric power. The contact elements 131 are enclosed in a housing 133 which is preferably designed as part of the insulator sleeve 126.

In addition, FIG. 4 shows four bores 127 extending axially through the body 110 of the magnetic flux element 109. These bores 127, the number, shape and diameter of which are of course variable, serve to conduct lubricant for components arranged in the hand-piece element 100 such as bearings or gears. The lubricants are introduced under pressure into the receptacle element 106 of the coupling 101 and flow through the bearing 116, the bores 127, the bearing 117 and, connected thereto, components of the hand-piece element 100 up to the head section 120.

The magnetic flux elements 114A additionally assume several bearing functions so that a compact design of the generator 103 and a space-saving installation in the hand-piece element 100 are possible. In first and second bearing points, which may be formed as a recess or a shoulder, the bearings 116, 117 are accommodated at least partially, with the bearings 116, 117 preferably rotatably supporting both the rotor 104 as well as the at least one shaft 102A of the drive element 102. A third and fourth bearing point of the magnetic flux element 114A, which may be designed, e.g., as a protrusion, a shoulder or a flange, accommodate at least parts of the stator 105, in particular the coils 112A, 112B. In addition, the coils 112A, 112B are preferably adhesively bonded to the magnetic flux element 114A or cast with it, e.g., with synthetic resin, especially epoxy resin. Finally, supporting surfaces or recesses are provided for O-rings 132 which support the generator 103 in the hand-piece element 100.

Due to the elongated axial design of the generator 103 with the long narrow magnetic elements 115, having an extent of approximately 1.2 mm×0.4 mm×6.2 mm, the coils 112A, 112B arranged axially in front of and behind the former, the magnetic flux elements 114A arranged axially in front of and behind the coils 112A, 112B and the sleeve-shaped magnetic flux element 114B, which is also long axially and narrow radially, this advantageously creates a generator, which can be installed in the hand-piece element 100 without resulting in an excessive increase in the diameter of the hand-piece element 100 and which supplies enough power for the consumer, in particular the lighting device 123.

FIGS. 3A and 3B show an alternative embodiment of a stator of the generator 103. With this stator 105' the magnetic flux element 134 is designed in one piece so the radial sleeve-shaped section 134A surrounding the rotor and the section 134B arranged axially in front of the rotor are made of one piece. The individual magnets 115 are in turn attached to the inside of the radial section 134A in a rotationally symmetrical manner. The single coil 112C is inserted into a receptacle of the magnetic flux element 134 and is preferably cast therein. The magnetic flux element 134 and the coil 112C each have a bore through which the shaft 102A of the drive element 102 can pass and into which at least parts of the rotor protrude. The axial section 134B in turn additionally assumes the function of a bearing seat for the bearing 117. A radial bore 135 which is provided in the magnetic flux element 134 has electric lines 124 passing through it for connection to the consumer. The advantage of the stator 105' is its more compact design and the resulting simplified installation in the generator 103 and the hand-piece element 100.

Figure 5:
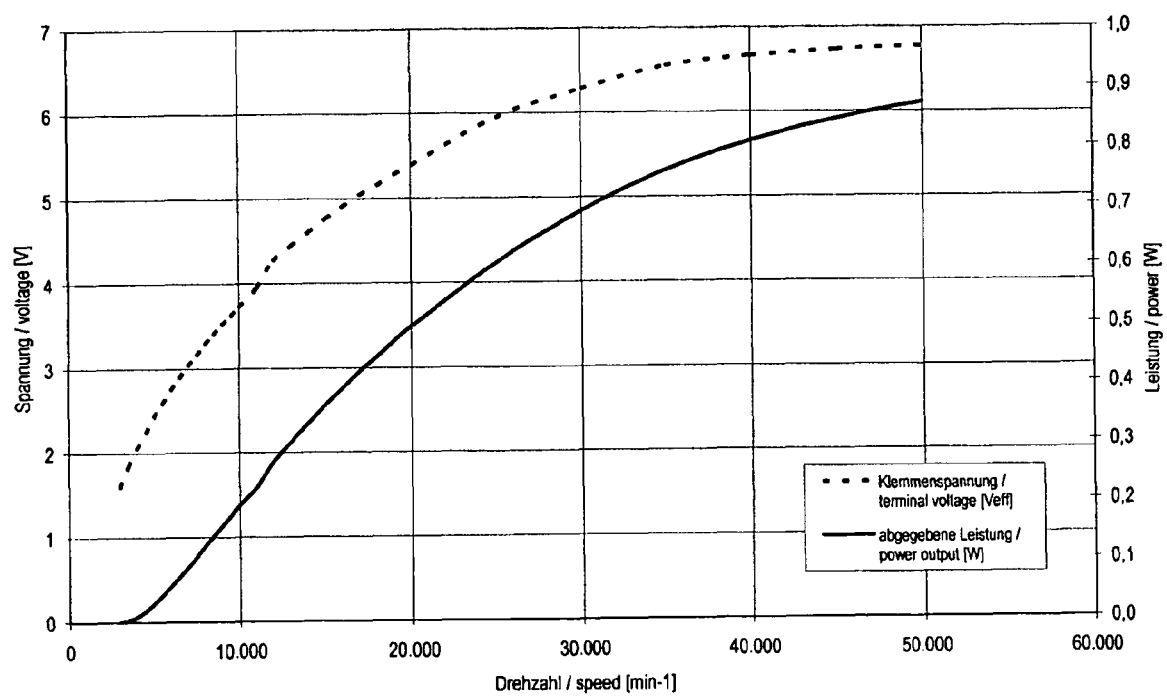
FIG. 5 shows a diagram with measured values for the terminal voltage and the power delivered by a generator according to FIG. 2.

FIG. 5 shows a diagram with measured values for the terminal voltage and the power delivered by the generator 103 which were determined at different rotational speeds of 3,000 to 50,000 rpm. In these measurements, an LED was connected to the generator as a consumer. Both the voltage and power curves have an approximately linear slope in the lower speed range from approximately 3,000 rpm up to the average speed range of approximately 25,000 revolutions per minute. In the subsequent rotational speed range of more than approximately 25,000 rpm, the slope of the two curves flattens out. The generator 103 thus has an optimal power performance for surgical application, in particular for a dental-surgical application.

Figure 6:
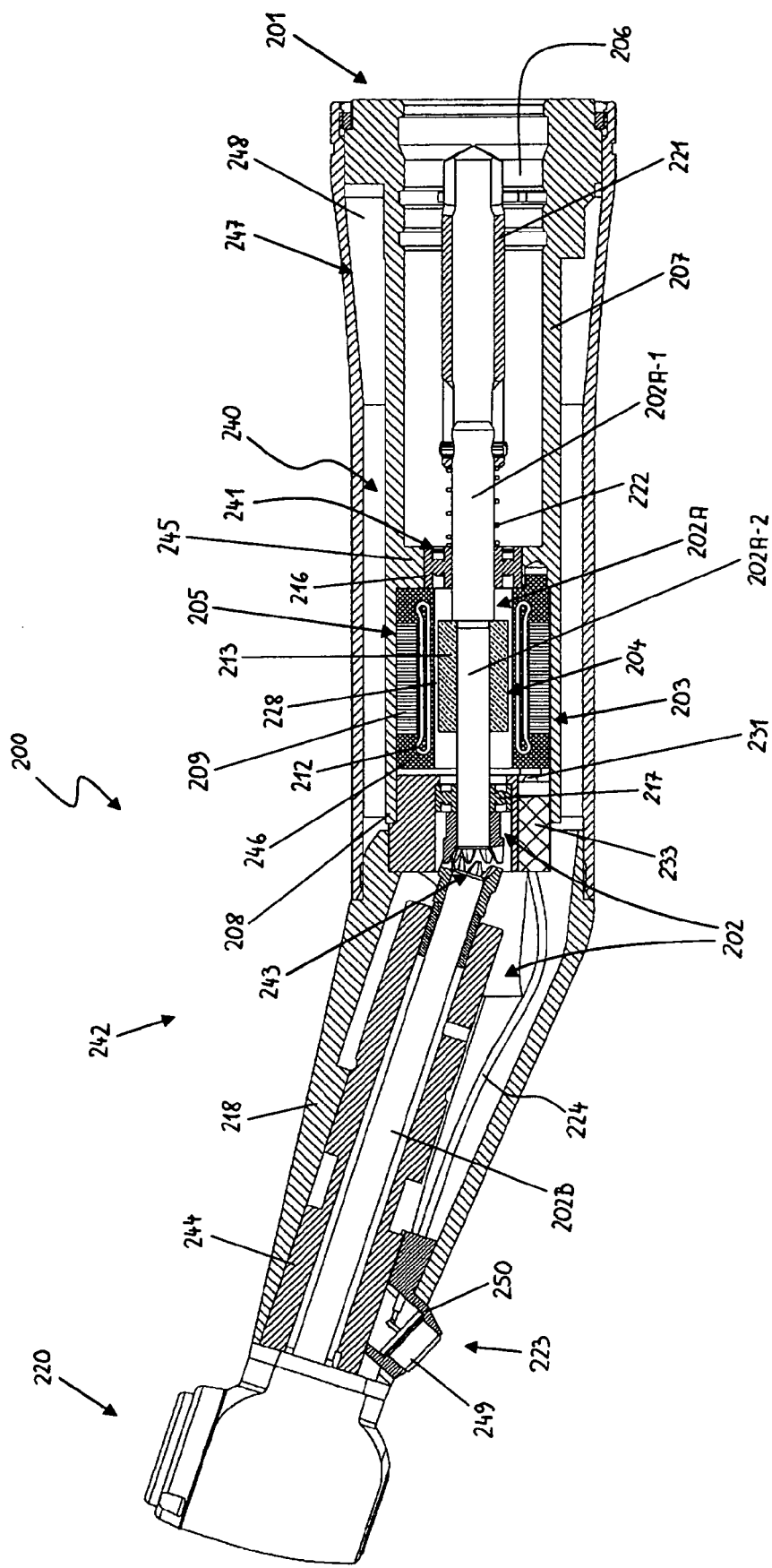
FIG. 6 shows an embodiment of a medical, in particular a dental hand-piece element with a generator.

The medical, in particular dental-medical hand-piece element 200 shown in FIG. 6 comprises a head section 220 and an elongated handle section 242 connected thereto. The hand-piece element 200 is designed as a so-called contra-angle hand-piece in which the handle section 242 consists of two parts arranged at an angle to one another and in which the tool opening is arranged at the side of the head section 220 so that a treatment tool can be inserted transversally to the handle section 242 into the head section 220. A multipart outer sleeve 218 surrounds the handle section 242 and head section 220. The hand-piece element may of course also have other external shapes, in particular a straight shape or a pistol shape.

In the front area or the head section 220 of the hand-piece element 200 there is a tool receptacle that is accessible via the opening in a known manner. The tool receptacle can then be accommodated at least partially in a hollow shaft which is movably mounted, in particular by means of two ball bearings. A gear wheel which meshes with a pinion or gear wheel of the drive element 202 is provided on the hollow shaft so that the driving movement can be transferred from the drive element 202 to the hollow shaft, and rotation of the hollow shaft together with the tool receptacle can be induced. Other mechanisms, e.g., an eccentric cam, may of course also be provided to induce other operating movements in the tool receptacle, e.g., a reciprocating, tumbling or oscillating movement.

The handle section 242 has the drive element 202 passing through it, such that the drive element 202 comprises a first shaft 202A and a second shaft 202B, which are interconnected via a gear 243 or gear wheels. The two shaft parts 202A, 202B are arranged at an angle to one another corresponding to the two angled sections of handle section 242. The shaft 202B is rotatably mounted in particular by friction bearings in a bearing bushing 244. The first shaft 202A is arranged closer to the coupling mechanism 201 than is the second shaft 202B. An entraining element 221 which is displaceably connected to the shaft 202A and is prestressed via a spring 222 is in turn connected to the shaft 202A.

The connection between the hand-piece element 200 and the drive unit for driving the tool receptacle and the tool is accomplished via a detachable coupling mechanism 201, which is preferably designed as a plug coupling or as a twist-lock plug coupling. For example, an air motor or an electric motor, in particular a brushless electric motor may be used as the drive unit. The drive unit may be connected directly to the hand-piece element 200, but it may also be connected to hand-piece element 200 indirectly via one or more intermediate pieces, such as adaptors or couplings. The coupling mechanism 201 comprises a receptacle element 206 which is designed as a cylindrical coupling tube 207, for example, to accommodate a coupling counterpart. At least one part of the shaft 202A and the entraining element 221 are accommodated in the interior of the receptacle element 206.

A generator 203 for converting mechanical energy into electric energy is provided in the hand-piece element 200, whereby the generator 203 can be driven by the shaft 202A of the drive element 202. The generator 203 has an essentially cylindrical exterior shape and is designed symmetrically about its longitudinal axis. The generator 203 and its rotor 204 in particular are arranged coaxially with the shaft 202A. In addition, the generator 203 is arranged essentially around the first shaft 202A and thus is closer to the coupling mechanism 201 so that the generator 203 is easy to replace. The receptacle element 206 which is designed as a cylindrical coupling tube 207 has a protrusion 208 which is also cylindrical and in which the generator 203 is accommodated. A first bearing point 216 for bearing of the shaft 202A and the rotor 204 of the generator 203 is provided on a ring shoulder 245 arranged between the receptacle element 206 and the protrusion 208. The second bearing point 217 is also situated in the protrusion 208. The generator 203 is arranged between the two bearing points 216, 217, which are preferably designed as ball bearings.

The rotor 204 of the generator 203, comprising a magnetic element 213 in the form of a two-pole permanent magnet, is mounted on the shaft 202. The magnetic element 213 is in the form of a hollow cylinder, with the shaft 202A passing through its inside bore. At least a part of the shaft 202A, in particular the part that is in the interior of the magnetic element 213, is manufactured of a magnetically conductive material for the purpose of achieving a better magnetic conductivity. The shaft 202A to which the magnetic element 213 is attached also has a first section 202A-1 with a first diameter and a second section 202A-2 with a second smaller diameter, wherein the magnetic element 213 is attached to the second section 202A-2. The diameter of the shaft section 202A-2 and the inside diameter of the inside bore of the magnetic element each amount to approximately 2.35 mm. The diameter of the shaft section 202A-1 amounts to approximately 3 mm. Due to the reduction in the diameter of the shaft section 202A-2 it is possible to increase the wall thickness of the magnetic element 213 to approximately 1.32 mm without having to increase its outside diameter of approximately 5 mm.

The stator 205 also surrounds the shaft 202A coaxially, separated by an air gap 228 from the rotor 204. The stator 205 comprises at least one, preferably several coils 212 and a magnetic flux element 209, which is designed as a laminated iron yoke, for example. The stator 205 is cast in a casting material 246, in particular a synthetic resin, e.g., epoxy resin and is sealed off from the environment so that the ambient conditions prevailing during a cleaning or sterilization procedure cannot attack or corrode the stator tool 5.

In addition, a cooling device 240 for dissipating at least a portion of the heat generated by the generator 203 is provided in the hand-piece element 200. The cooling device 240 comprises the receptacle element 206 of the coupling mechanism 201 as well as the protrusion 208 connected thereto. The generator 203 is in direct contact with the protrusion 208 which is made of a material, especially metal, that conducts heat well, so that the heat is dissipated away from the generator 203 via the protrusion 208 and the coupling tube 207.

The cooling device 240 in addition has a connection 241 between the coupling mechanism 201, in particular the receptacle element 206, and the generator 203 so that a cooling medium, in particular cooling air can be supplied to the generator 203 via the coupling mechanism 201. The connection 241 preferably connects the air gap 228 of the generator 203 to the coupling mechanism 201 so that heat is also dissipated from the interior of the generator. The connection between the generator 203 and the coupling mechanism 201 preferably accomplished via gaps or clearances in or between the components of the hand-piece element 200, e.g., through the ball bearing 216. This yields a simple design of the connection 241 and in particular no separate cooling media lines are required.

To further reduce the heat transfer from the generator 203 to the outer sleeve 218, thermal insulation means 247 are provided between the generator 203 and the outer sleeve 218. These insulation means 247 may comprise, for example, an air gap 248 between the outer sleeve 218 and the generator 203 and/or insulation means provided between the outer sleeve 218 and the generator 203, e.g., foamed plastics or organic insulation materials.

The generator 203 is connected by electric lines 224 to a consumer, e.g., a lighting device 223. The electric power generated by the generator 203 is supplied to electric contact elements 231 and lines 224 to supply the consumer via the free ends of the two coils 212. The contact elements 231 are preferably enclosed in a housing 233 and are hermetically sealed from the environment so they can resist the conditions that prevail during cleaning or sterilization.

The lighting device 223 preferably comprises one or more optical semiconductor components, e.g., LEDs. The semiconductor component is preferably enclosed in a hermetically sealed capsule 249 with an interior that is completely sealed off from the environment. Therefore the lighting device 223 can also be sterilized. The capsule 249 has a transparent area at least on its side facing away from the hand-piece element 200, such that the light generated by the semiconductor component can be emitted through this transparent area to the environment. The lighting device 223 is accommodated in an opening in the outer sleeve 218 near the head section 220 and/or protrudes at least partially out of this opening and is oriented in such a way that its light is emitted approximately toward the tip of the tool and the preparation site. As an alternative, the lighting device 223 may also be mounted in or on the head section 220, preferably around the tool opening.

For a fixation in the hand-piece element 200, the capsule 249 and the semiconductor component are accommodated in a holder 250. The electric contacts of the semiconductor component and the ends of the lines 224 connected to them protrude into an interior space of the holder 250 which is filled with a casting material, in particular a synthetic resin such as epoxy resin. The holder 250 is inserted through a plug connection in the opening of the outer sleeve 218, for example or as an alternative or in addition it may also be held in this opening by bearing sleeve 244.

The contacts 231 are preferably designed to be releasable, e.g., as plug contacts so that the generator 203 or the lighting device 223 can be removed from the hand-piece element 200 independently of one another for the purpose of maintenance or replacement. The generator 203 is removed from the hand-piece element 200 by releasing and extracting the coupling tube 207 and its protrusion 208 out of the outer sleeve 218 of the hand-piece element 200. Then the generator 203 can be removed from the protrusion 208. The rotor 204 and stator 205 are preferably designed as modules that are separable from one another and thus can be replaced independently of one another.

Figure 7:
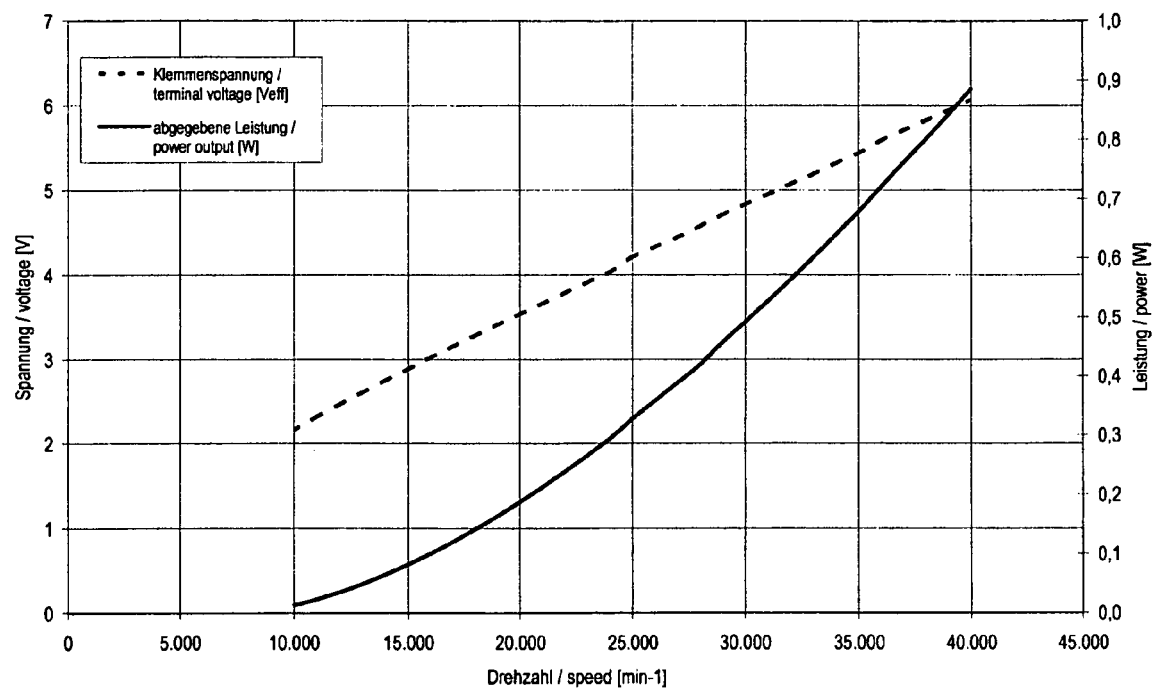
FIG. 7 shows a diagram with measured values for the terminal voltage and the power delivered by a generator according to FIG. 6.

FIG. 7 shows a diagram with measured values for the terminal voltage and the power delivered by the generator 203 which were determined at different rotational speeds of 10,000 to 40,000 rpm. In these measurements an LED as a consumer was connected to the generator. Both the voltage curve and the power curve show approximately a linear slope over the entire rotational speed range. Above a rotational speed range of approximately 20,000 revolutions per minute, the power delivered by the generator 203 is sufficient to supply an LED.

This invention is not limited to the embodiments described here but instead includes all possible embodiments that do not alter the basic appropriate function principle of the invention.

What is claimed is:

1. A medical hand-piece element, comprising:
 a coupling mechanism for releasable connection of the hand-piece element to a drive unit,
 a tool receptacle,
 a drive element for transmitting a driving movement from the drive unit to the tool receptacle so that the tool receptacle can be set in a working movement,
 wherein the drive element extends into the coupling mechanism and has a proximal end drivingly engageable with a coupling counter part of the drive unit to transmit the driving movement for the tool receptacle,
 wherein the drive element comprises a first shaft and a second shaft which are connected to one another by a geared connection and wherein the first shaft is arranged closer to the coupling mechanism than is the second shaft, and a generator for converting mechanical energy into electric energy,
 wherein the generator is arranged substantially around the first shaft and can be driven by the first shaft of the drive element, and
 wherein the generator is arranged in a receptacle element which is connected to the medical hand-piece element such that the receptacle element contacts only inner surfaces of the hand-piece element.

2. The hand-piece element according to claim 1, wherein the generator comprises a rotor and a stator and wherein at least the rotor is arranged coaxially with the first shaft of the drive element.

3. The hand-piece element according to claim 1, wherein the coupling mechanism comprises the receptacle element, in particular a coupling tube to accommodate a coupling counterpart, and wherein the generator is arranged at least partially in or on the receptacle element or in or on a protrusion of the receptacle element.

4. The hand-piece element according to claim 1, wherein the generator comprises a rotor and a stator, wherein the stator comprises at least one coil and one or more magnetic elements and wherein the rotor comprises a magnetic yoke element which is surrounded by the one or more magnetic elements of the stator and which is configured to direct magnetic lines of the one or more magnetic elements around and through the at least one coil of the stator.

5. The hand-piece element according to claim 4, wherein the magnetic yoke element of the rotor has a central body from which several protrusions protrude radially, separated from one another by interspaces.

6. A medical hand-piece element, comprising:
 a coupling mechanism for releasable connection of the hand-piece element to a drive unit,
 a tool receptacle connected to the hand-piece element,
 a drive element for transmitting a driving movement from the drive unit to the tool receptacle so that the tool receptacle can be set in a working movement, wherein the drive element comprises at least one rotatable shaft and wherein the drive element extends into the coupling mechanism, so that the drive element can engage a coupling counter part of the drive unit in order to take over the driving movement for the tool receptacle, and a generator for converting mechanical energy into electric energy, wherein the generator can be driven by the at least one rotatable shaft of the drive element, wherein the generator comprises a rotor and a stator, wherein the stator comprises at least one coil and one or more magnetic elements and wherein the rotor comprises a magnetic yoke element which is surrounded by the one or more magnetic elements of the stator and which is configured to direct magnetic lines of the one or more magnetic elements around and through the at least one coil of the stator, and wherein the stator comprises at least one additional magnetic yoke element which produces a magnetic return of the magnetic lines of the one or more magnetic elements around and through the at least one coil of the stator.

7. A medical hand-piece element, comprising:

a coupling mechanism for releasable connection of the hand-piece element to a drive unit, a tool receptacle connected to the hand-piece element, a drive element for transmitting a driving movement from the drive unit to the tool receptacle so that the tool receptacle can be set in a working movement, wherein the drive element comprises at least one rotatable shaft and wherein the drive element extends into the coupling mechanism, so that the drive element can engage a coupling counter part of the drive unit in order to take over the driving movement for the tool receptacle, and a generator for converting mechanical energy into electric energy, wherein the generator can be driven by the at least one rotatable shaft of the drive element, wherein the generator comprises a rotor and a stator, wherein the stator comprises at least one coil and one or more magnetic elements and wherein the rotor comprises a magnetic yoke element which is surrounded by the one or more magnetic elements of the stator and which is configured to direct magnetic lines of the one or more magnetic elements around and through the at least one coil of the stator, and wherein the one or more magnetic elements have multiple permanent magnets or permanent magnet regions and wherein the permanent magnets or permanent magnet regions are arranged side-by-side and have an alternating polarity.

8. The hand-piece element according to claim 7, wherein the magnetic yoke element of the rotor has a central body from which several protrusions protrude radially, separated from one another by interspaces.

9. The hand-piece element according to claim 6, wherein the at least one additional magnetic yoke element of the stator has a bearing function for the rotor and the at least one shaft of the drive element.

10. The hand-piece element according to claim 6, wherein the at least one additional magnetic yoke element of the stator has a bearing function for at least part of the stator.

11. The hand-piece element according to claim 1, wherein the generator has a rotor and a stator, wherein the rotor comprises a magnetic element which is attached to the first shaft of the drive element and wherein at least a part of the first shaft is made of a magnetically conductive material.

12. The hand-piece element according to claim 1, wherein the generator has a rotor and a stator, wherein the rotor comprises a magnetic element which is attached to the first shaft of the drive element and wherein the first shaft, to which the magnetic element is attached comprises a first section having a first diameter and a second section having a second diameter smaller than the first diameter and wherein the magnetic element is attached to the second section.

13. The hand-piece element according to claim 1, wherein the generator comprises a rotor and a stator, wherein the rotor comprises a magnetic element which is mounted on the first shaft of the drive element, wherein the first shaft is mounted on two bearing points and wherein the magnetic element is arranged between the two bearing points.

14. The hand-piece element according to claim 1, further comprising a cooling device for dissipating heat generated by the generator.

15. The hand-piece element according to claim 14, wherein the cooling device comprises a connection between the coupling mechanism and the generator so that a cooling medium can be supplied to the generator via the coupling mechanism.

16. The hand-piece element according to claim 15, wherein the connection connects at least an air gap of the generator to the coupling mechanism.

17. The hand-piece element according to claim 14, wherein the cooling device comprises the receptacle element or at least one media line.

18. The hand-piece element according to claim 1, further comprising an energy storage mechanism that is connectible to the generator.

19. The hand-piece element according to claim 1, further comprising a device for dissipation of energy that is connectible to the generator.

20. The hand-piece element according to claim 1, wherein the generator is designed so that it can be sterilized repeatedly, wherein the generator comprises a stator which is cast in a casting material in order to seal off the stator so that conditions prevailing during a sterilization procedure cannot attack or corrode the stator and wherein the rotor is arranged inside of the sealed off stator.

21. The hand-piece element according to claim 1, wherein the generator is electrically connectible to at least one optical semiconductor component for emission of visible light, so that the at least one optical semiconductor component can be supplied with electric energy via the generator, wherein the at least one optical semiconductor component is arranged on the hand-piece element such that its light is emitted toward a tool received in the tool receptacle or toward the preparation site.

22. A medical hand-piece element comprising:

a tool receptacle, a drive element for transmitting a driving movement to the tool receptacle so that the tool receptacle can be set in a working movement, wherein the drive element comprises at least one rotatable shaft, and a generator for converting mechanical energy into electric energy, wherein the generator can be driven by the at least one rotatable shaft of the drive element, wherein the generator comprises a rotor and a stator, wherein the stator comprises at least one coil and a magnetic element and wherein the rotor comprises a magnetic yoke element which is surrounded by the magnetic element of the stator and which is configured to direct magnetic lines of the magnetic element of the stator around and through the at least one coil of the stator, so that by the rotation of the rotor the generator generates an alternating voltage, and wherein the magnetic element comprises multiple permanent magnet ranges or multiple individual permanent magnets which are arranged in a rotationally symmetrical arrangement and with alternating polarities.

23. The hand-piece element according to claim 21, wherein the at least one optical semiconductor component is designed so that it can be sterilized repeatedly.

24. The hand-piece element according to claim 22, wherein the magnetic yoke element of the rotor has a central body from which several protrusions protrude radially, separated from one another by interspaces.

25. The hand-piece element according to claim 24, wherein the central body and the several protrusions of the magnetic yoke element of the rotor are made of a magnetically conductive material and wherein there is no conductive material in the interspaces which separate the several protrusions of the magnetic yoke element of the rotor.

26. The hand-piece element according to claim 6, wherein the magnetic yoke element of the rotor has a central body from which several protrusions protrude radially, separated from one another by interspaces.

27. The hand-piece element according to claim 26, wherein the central body and the several protrusions of the magnetic yoke element of the rotor are made of a magnetically conductive material and wherein there is no conductive material in the interspaces which separate the several protrusions of the magnetic yoke element of the rotor.

28. The hand-piece element according to claim 8, wherein the number of permanent magnets or permanent magnet regions is twice as great as the number of radial protrusions on the magnetic yoke element of the rotor.

29. The hand-piece element according to claim 8, wherein the central body and the several protrusions of the magnetic yoke element of the rotor are made of a magnetically conductive material and wherein there is no conductive material in the interspaces which separate the several protrusions of the magnetic yoke element of the rotor.

30. The hand-piece element according to claim 6, wherein the generator is electrically connectible to at least one optical semiconductor component for emission of visible light, so that the at least one optical semiconductor component can be supplied with electric energy via the generator, wherein the at least one optical semiconductor component is arranged on the hand-piece element such that its light is emitted toward a tool received in the tool receptacle or toward the preparation site and wherein the at least one optical semiconductor component is designed so that it can be sterilized repeatedly.

31. The hand-piece element according to claim 22, wherein the generator is electrically connectible to at least one optical semiconductor component for emission of visible light, so that the at least one optical semiconductor component can be supplied with electric energy via the generator, wherein the at least one optical semiconductor component is arranged on the hand-piece element such that its light is emitted toward a tool received in the tool receptacle or toward the preparation site and wherein the at least one optical semiconductor component is designed so that it can be sterilized repeatedly.

32. The hand-piece element according to claim 1, wherein at least the first shaft of the drive element comprises a shaft connecting element positioned at each end of the first shaft and configured for connecting each end to another shaft.

33. A medical hand-piece element, comprising:
a coupling mechanism for releasable connection of the hand-piece element to a drive unit,
a tool receptacle,
a drive element for transmitting a driving movement from the drive unit to the tool receptacle so that the tool receptacle can be set in a working movement, wherein the drive element comprises at least one rotatable shaft,
a generator for converting mechanical energy into electric energy, wherein the generator can be driven by the at least one rotatable shaft of the drive element, and
a cooling receptacle for dissipating heat generated by the generator, wherein the cooling receptacle comprises a passageway extending between the coupling mechanism and the generator through which air that has cooled the drive unit is received in the cooling receptacle through the coupling mechanism and can be supplied to the generator to cool the generator.

34. The hand-piece element according to claim 33, wherein the passageway connects at least an air gap of the generator to the coupling mechanism.

35. The hand-piece element according to claim 33, wherein the cooling receptacle accommodates the generator and/or at least one media line.

36. The hand-piece element according to claim 33, wherein the drive element comprises a first shaft and a second shaft which are connected to one another by a geared connection, wherein the first shaft is arranged closer to the coupling mechanism than is the second shaft, and wherein the generator is arranged substantially around the first shaft and can be driven by the first shaft of the drive element.

37. The hand-piece element according to claim 33, wherein the generator is designed so that it can be sterilized repeatedly.

38. The hand-piece element according to claim 33, wherein the generator is electrically connectible to at least one optical semiconductor component for emission of visible light, so that the at least one optical semiconductor component can be supplied with electric energy via the generator.

39. The hand-piece element of claim 33, further comprising a drive unit in a form of an air-cooled electric motor, and wherein the air-cooled electric motor supplies air to the cooling receptacle to cool the generator.

* * * * *